United States Patent [19]
Juvinall

[11] 3,941,686
[45] Mar. 2, 1976

[54] INSPECTION MACHINE MEMORY

[75] Inventor: John W. Juvinall, Toledo, Ohio

[73] Assignee: Owens-Illinois, Inc., Toledo, Ohio

[22] Filed: Mar. 27, 1975

[21] Appl. No.: 562,989

[52] U.S. Cl. ........... 209/74 M; 340/259; 235/92 SH; 340/173 FF
[51] Int. Cl.² ........................................... B07C 5/00
[58] Field of Search ................... 209/74, 74 M, 75; 250/223 B; 340/259, 173 FF; 235/92 SH, 151–153

[56] References Cited
UNITED STATES PATENTS
3,757,940   9/1973   Damm ............................. 209/74 M

*Primary Examiner*—Allen N. Knowles
*Attorney, Agent, or Firm*—Steve M. McLary; Edward J. Holler

[57] ABSTRACT

An improved memory for a glass container inspection machine. In one common form of glass container inspection machines, the containers are indexed through multiple stations where they are inspected for various attributes. Rejection of defective containers can take place only after all of the inspections have been made. The information relative to a defective container is placed in a master-slave type flip-flop uniquely associated with a particular inspection station. Information is then shifted through a group of series-connected master-slave type flip-flops in synchronism with the movement of the container until the container, if defective, reaches a location where it can be rejected. The information is moved or clocked by a generated clock pulse that has a rise time that is faster than the information transfer time through the flip-flops.

6 Claims, 2 Drawing Figures

INSPECTION MACHINE MEMORY

BACKGROUND OF THE INVENTION

This invention relates to a memory for a glass container inspection machine. More particularly, this invention relates to a memory for a glass container inspection machine which indexes glass containers from station to station for inspection. Specifically, this invention relates to a solid state memory for such an inspection machine.

One well-known type of inspection machine for glass containers is that known as the FP machine, manufactured by Owens-Illinois, Inc. This is a rotary, indexing machine where glass containers are indexed through a plurality of stations for inspection. A defect may be found at any station, but rejection of a defective container cannot occur until the last inspection station has been passed. Thus, these machines require a memory to allow retention of defective container information until a rejection location is reached. In the past, pin-type or magnetic belt memories have been used. However, these are basically mechanical devices which have presented not only maintenance problems but also accuracy of information storage problems. I have devised a solid state memory for this machine which uses reliable, durable electronic components. This reduces maintenance problems and raises the reliability with which the memory is retained. A very fast clock pulse is used to clock a group of series-connected flip-flops in a time less than the transfer time of information through the flip-flops.

Memory systems of this general type are not unknown in the prior art. For example, see U.S. Pat. Nos. 3,259,240; 3,263,810; 3,565,249; and 3,581,889. The best example of the prior art known to me is U.S. Pat. No. 3,757,940. This patent teaches a solid state memory for a similar FP type machine. The memory of the cited patent has been successful, but it is quite complex and is designed for very high speed operation. It requires two memories and two separate clock frequencies to allow downstream rejection of the defective containers. In addition, the clock pulses must be delayed and conditioned to avoid false shifts of information. My invention is designed for FP machines which operate at moderate speeds and do not require downstream rejection. In addition, I have simplified the circuit of the cited patent and eliminated the need for delay and conditioning of the clock pulses. Furthermore, my clock pulse generation technique is much simpler since only a single clock pulse at a single frequency is required.

SUMMARY OF THE INVENTION

My invention resides in an inspection machine for glass containers. In this machine, the glass containers are removed one at a time from a continually moving conveyor and serially indexed through a plurality of inspection stations. The inspection machine includes a bottle defect logic and detection means which generates output signals if the inspected glass containers are defective in one or more aspects at any one of the inspection stations. My invention is specifically an improved memory for this machine. A plurality of master-slave type flip-flops are connected in series, with the number of flip-flops being one more than the number of inspection stations. Means are provided for connecting an output conductor from the logic means to each one of the flip-flops except the last one of the plurality of flip-flops. A timing means presents a first electrical state when the inspection machine is inspecting and a second electrical state when the inspection machine is in its index cycle. An electronic clock circuit means generates a clock pulse having a rise time faster than the information transfer time through any one of the flop-flops in response to the transition of the timing means from the second electrical state to the first electrical state. The clock circuit means is connected to the timing means and each of the flip-flops. An electronic output circuit means generates a signal when the last of the plurality of flip-flops carries a signal indicating the presence of a defective glass container and when the clock pulse is present. The output circuit means is connected to an output terminal of the last flip-flop and the clock circuit means.

DETAILED DESCRIPTION OF THE DRAWINGS

Figure 1:
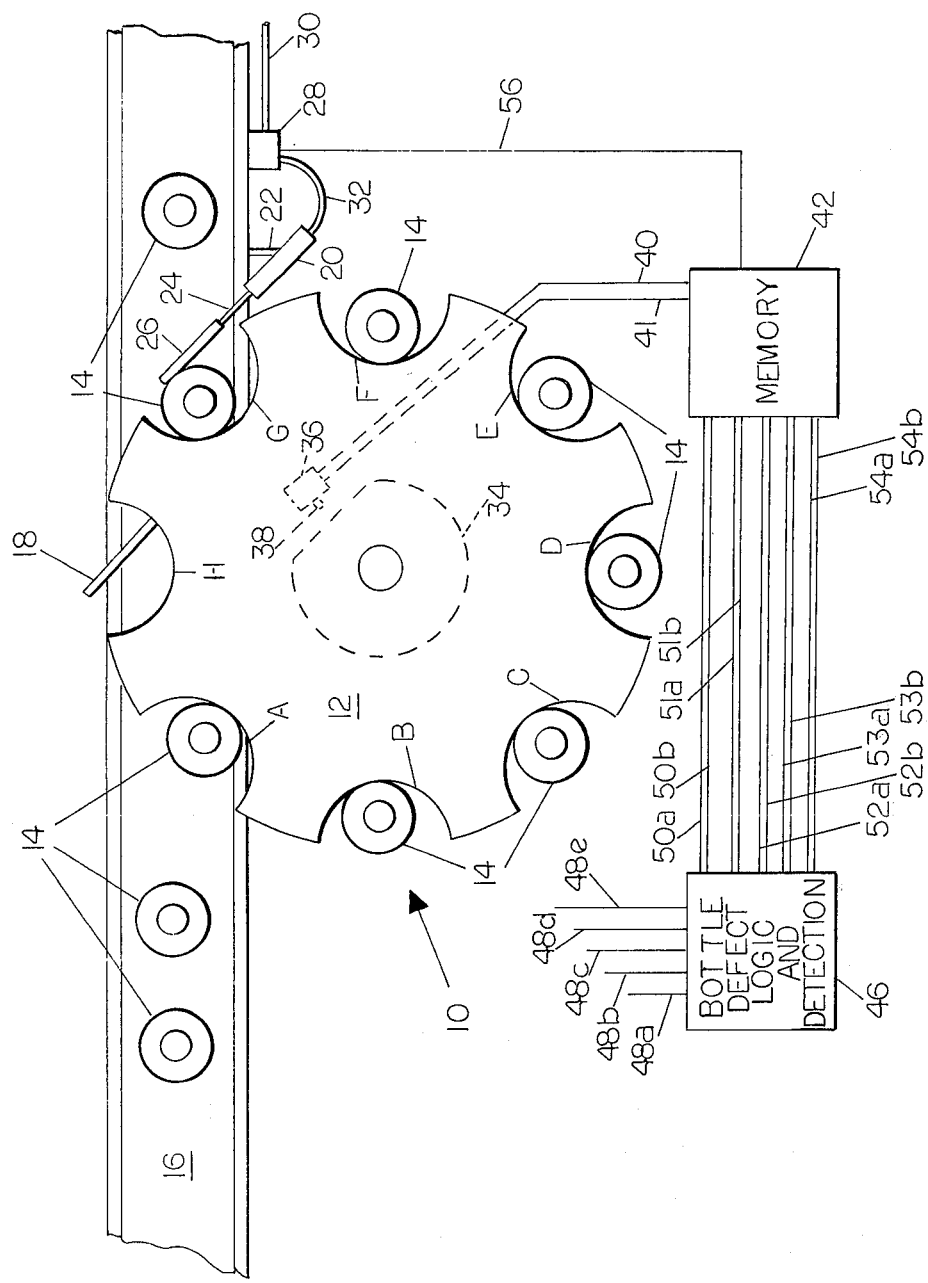
FIG. 1 is a schematic top plan view showing the interrelation of the present invention with a glass container inspection machine.

FIG. 1 shows the mechanical and electronic apparatus of the present invention in a schematic form. The present invention is designed specifically to operate with a bottle gauging apparatus such as that described in U.S. Pat. No. 3,313,409 the teachings of which are hereby incorporated by reference. It is believed that the teachings of the cited patent are sufficiently clear to allow one skilled in the art to utilize the present invention when described in a schematic form. A gauging apparatus or article inspection machine is generally designated by the numeral 10. The inspection machine 10 includes a rotatable disk 12 having pockets cut therein for receiving glass containers 14 to be inspected. The glass containers 14 are presented to the inspection machine 10 in a single file by a continually moving conveyor 16. The conveyor 16 also serves to remove the articles from the gauging machine 10. The conveyor 16 thus serves as a means for delivering and removing articles from the gauging apparatus 10. As taught in U.S. Pat. No. 3,313,409, the glass container 14 which is positioned in the pocket designated as A is sequentially rotated or indexed to positions or stations designated as B, C, D, E and F. Inspection of the glass container 14 is carried out at positions B, C, D, E and F by apparatus which is not shown but which is well known to those skilled in the art. Position G is a position in which a container 14 is held prior to its release to the conveyor 16. If the container 14 has been passed by all the inspections performed upon it during its indexing from station to station, the container 14 is released and allowed to proceed down the conveyor 16. If the container 14 has shown some defect, it is rotated toward the position noted as H. However, a diverter bar 18 sweeps the container 14 off the conveyor 16 and into a rejection area before it can complete the index and then be further indexed to position A where it would interfere with incoming containers 14. At station G, an air motor 20, supported from the conveyor 16 by a suitable bracket 22, serves to control the release of containers to the conveyor 16 and for holding defective conveyors for rejection by the diverter bar 18. The air motor 20 includes an extensible operating rod 24 which carries on its end a tip 26. The tip 26 is retracted or removed from contact with the glass container 14 by retraction of the operating rod 24 in response to a signal indicating that a glass container 14 has passed all of the inspections performed upon it in the inspection machine 10. If the glass container 14 has proven defective in one or more attributes, the operating rod 24 is not retracted and consequently the tip 26 prevents the glass container 14 from moving along the conveyor 16. Then, the next index cycle of the inspection machine 10 forces the container 14 into contact with the diverter bar 18 for rejection. The operation of the air motor 20 is controlled by a solenoid valve 28 which is furnished a source of air under pressure from a source not shown through a pipeline 30. This air is then selectively supplied to the air motor 20 through a pipeline 32. As is well known in these general types of inspection machines 10, the glass containers 14 are indexed from station to station in a controlled manner by an indexing drive. A rotary cam 34 is driven in a continuously rotating fashion by the main machine drive. This cam 34 is thus in synchronism with the indexing drive and can be used to provide timing signals. While the disk 12 is driven in an intermittent, indexing mode, the cam 34 rotates continuously and makes one complete revolution for each cycle of the disk 12, one cycle including an inspection mode when the disk 12 is stopped and an index mode when the disk 12 is moved. In fact, a switch 36, which has an operating plunger 38, is positioned in proximity to the cam 34 so that the cam 34 operates the plunger 38 of the switch 36 and thus generates electrical timing signals along two output conductors 40 and 41. The conductors 40 and 41 carry information from the switch 38 indicating whether the machine is in the inspection mode or in the indexing mode. The information is carried in terms of two different electrical states of the switch 36 and the cam 34 and switch 36 therefore form a means to present these two states. The conductors 40 and 41 are connected to a main machine memory 42. The bottle defect logic and detection unit 46 is of the type well known in the art and may be of that type as shown in U.S. Pat. No. 3,313,409. Signals from the detection equipment mounted above or below the rotatable disk 12 are fed into the logic unit 46 through five input conductors 48a, b, c, d and e. It is possible for a glass container 14 to be inspected for multiple attributes at any one of the stations B through F. It should be quite evident that a glass container 14 may be found defective at any one of the inspection stations B, C, D, E or F. However, implementation of the decision to reject such a defective glass container 14 cannot be made until station G is reached. Therefore, the memory 42 serves the function of maintaining the information which indicates that a particular glass container 14 is defective and processing this information so that any glass container which exhibits a defect in any one of the inspection stations will be rejected at stations G and F. To this end, five separate sets of conductors 50a and b, 51a and b, 52a and b, 53a and b, and 54a and b carry defective bottle information from the bottle defect logic and detection unit 46 to the memory 42. Then, at the proper time, a signal is transmitted from the memory 42 through an electrical conductor 56 to the solenoid valve 28 to cause cycling of the solenoid valve 28 to either accept or reject a glass container 14 presented at station G.

Figure 2:
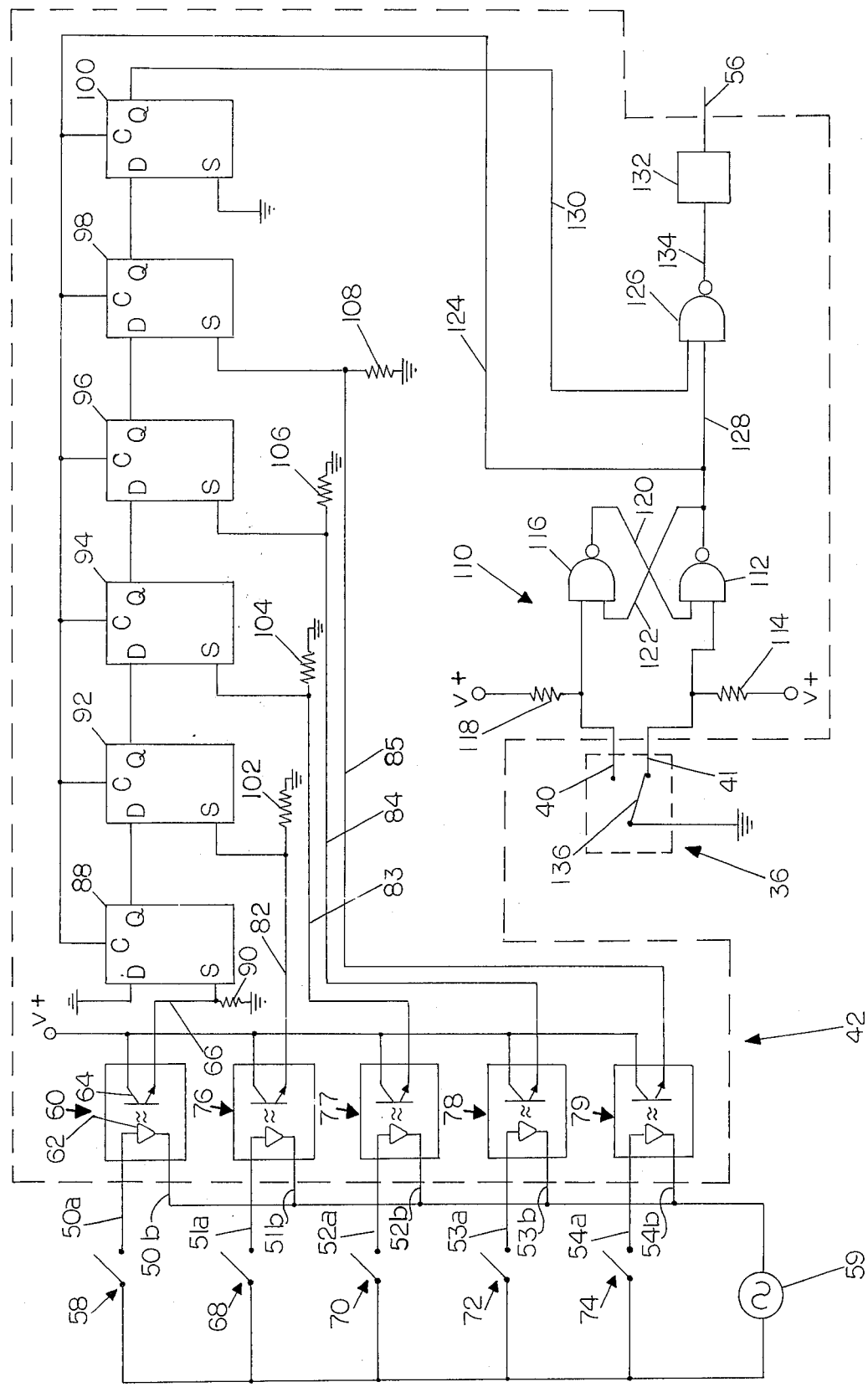
FIG. 2 is a block diagram of the memory of the present invention.

FIG. 2 shows the construction of the memory unit 42 in a block diagram form. The conductors 50a and 50b are connected to a normally open relay 58 which is a part of the bottle defect logic and detection unit 46. When a defective glass container 14 has been detected at station B, the relay 58 will close in response thereto and therefore complete a circuit with the conductors 50a and 50b. The circuit is completed with an optical isolator 60. The optical isolator 60 is of a generally conventional type which contains within it a photo-diode 62 which is connected in series with the conductors 50a and 50b and the relay 58, and a photo-transistor 64 whose base is positioned to receive light energy from the photo-diode 62 when it is turned on. In operation, closing of the relay 58 will allow power to flow through the conductors 50a and 50b, noting that the conductors 50a and 50b are connected across a voltage supply 59, noted by way of illustration as an AC source, thereby energizing the photo-diode 62. This in turn will allow the photo-transistor 64 to generate an output signal from its emitter along a conductor 66. Note that the collector of photo-diode 64 is connected to the positive voltage supply of the circuit. In a similar fashion, the conductors 51a and 51b are connected to a relay 68, the conductors 52a and 52b to a relay 70, the conductors 53a and 53b to a relay 72, and the conductors 54a and 54b to a relay 74. The relays 68, 70, 72 and 74 are also connected to the voltage supply 59 in the same manner as the relay 58. The relays 68, 70, 72 and 74 correspond to the inspection stations C, D, E and F and will be closed in response to a defective glass container 14 being detected at these stations. As was the case with the first pair of conductors 50a and 50b, all the other conductors 51a through 54b are connected to respective optical isolators 76, 77, 78 and 79. The operation and functioning of the optical isolators 76 through 79 is identical to that described with respect to the optical isolator 60 and further detailed discussion is believed unnecessary. In addition, all of the photo-transistors in the optical isolators 76 through 79 have their collectors connected to the positive voltage supply of the circuit. In a similar manner, each of the optical isolators 76 through 79 present individual outputs from their emitters on respective conductors 82, 83, 84 and 85. Of course it is understood that these output signals will be generated on these conductors only when a signal has been received from the appropriate inspection station indicating the presence of a defective glass container 14. The conductor 66 from the optical isolator 60 is connected to the direct set input of a first flip-flop 88. The flip-flop 88 contains in addition to the direct set input a conditional set input S, a clock input C and an output terminal Q. The flip-flop 88 is preferably a model CD4013 AE manufactured by the RCA Corporation. This particular type of flip-flop is of the master-slave type which indicates that internally there is a two-stage transfer of information from the D terminal to the Q terminal before the Q terminal will display information presented to the D terminal. This function is of importance in that there is a delay in propagation of information through the flip-flop 88. This particular property will be taken advantage of as will be described later. It is possible that other types of flop-flops could be used, and the conditions for their use will be described with respect to the description of the clocking of the flip-flops. The D terminal of the first flip-flop 88 is connected to ground to assure that no spurious or false inputs are placed in this particular unit. The only input to the first flip-flop 88 is through the direct set terminal S and is from the optical isolator 60. Thus a signal to the first flip-flop 88 indicates that a defective glass container 14 has been detected at inspection station B. In order to present a consistent signal to the flip-flop 88 when no signal is present from the optical isolator 60, the S terminal of the first flip-flop 88 is also connected to ground through a resistor 90. The Q output terminal of the first flip-flop 88 is connected to the D or conditional set terminal of a second flip-flop 92 which is identical to the first flip-flop 88. Similarly, the Q output terminal of the second flip-flop 92 is connected to the D input terminal of a third flip-flop 94. The Q output terminal of the third flip-flop 94 is connected to the D input terminal of a fourth flip-flop 96. The fourth flip-flop 96 has its Q output terminal connected to the D input terminal of a fifth flip-flop 98. The fifth flip-flop 98 has its Q output terminal connected to the D input terminal of a sixth and final flip-flop 100. There are therefore in total six flip-flops, five of which are used to store information relative to defective bottles which are detected at stations B, C, D, E and F. The second flip-flop 92 has its S terminal connected to the conductor 82 which carries information from the optical isolator 76 relative to defects occurring at station C. As was the case with the first flip-flop 88, the second flip-flop 92 also has its S terminal connected to ground through a resistor 102. The third flip-flop 94 has its S terminal connected to the conductor 83 which carries information from the optical isolator 77 indicating the presence of a defective glass container 14 at station D. A resistor 104 connects the S terminal of the third flip-flop 94 to ground. The fourth flip-flop 96 has its S terminal connected to the conductor 84 which in turn carries a signal from the optical isolator 78 which will indicate the presence of a defective glass container at station E. A resistor 106 connects the S terminal of the fourth flip-flop 96 to ground. The fifth flip-flop 98 is the final unit which actually receives direct information relative to the detection of a defective glass container during the inspection cycle. The conductor 85 is connected to the S terminal of the fifth flip-flop 98 and carries information from the optical isolator 79 indicating the detection or presence of a defective glass container at inspection station F. A resistor 108 connects the S terminal of the fifth flip-flop 98 to ground. The sixth flip-flop 100 is a final output flip-flop which carries the total sum of the information which has been stored in the preceding five flip-flops. Its S terminal is connected to ground directly to prevent entry of any signal into this particular terminal of the flip-flop 100. This is necessary because any information entered into the flip-flop 100 must be information which has been passed through the preceding flip-flops in series. It should therefore be clear from this arrangement and connection of units that any signal indicating the presence of a defective glass container 14 at any one of the inspection stations is independently entered into its respective flip-flop at the time this defect is detected. This information is then shifted in sequence as this particular glass container is indexed from station to station until the information finally enters the final flip-flop 100. At this time, the decision must be made whether to accept or reject the glass container 14 which has been passed through the entire inspection machine 10. An anti-bounce fast-rise time circuit 110 is used to provide a very fast rising clock pulse and to overcome any tendency of the switch 36 to bounce during its cycle. As is evident in FIG. 2, the switch 36 is connected to ground and has two separate terminals, one connected to the output conductor 40 and the other connected to the output conductor 41. The output conductor 41 connected to one input terminal of a first NAND gate 112. The conductor 41 is also connected to the positive voltage supply v plus of the circuit through a resistor 114. The conductor 40 is connected to one input terminal of a second NAND gate 116. The conductor 40 is also connected to the positive voltage supply of the circuit through a resistor 118. The output terminal of the second NAND gate 116 is connected to a second input terminal of the first NAND gate 112 by a conductor 120. The output of the first NAND gate 112 is connected to a second input of the second NAND gate 116 through a conductor 122. The output of the first NAND gate 112 is also connected to the C or clocking input terminal of all of the flip-flops 88, 92, 94, 96, 98 and 100 through a conductor 124. The output of the first NAND gate 112 is also connected to one input terminal of a third NAND gate 126 by a conductor 128. The Q output terminal of the final flip-flop 100 is connected to a second input terminal of the third NAND gate 126 by a conductor 130. The output terminal of the third NAND gate 126 is connected to a control relay 132 by a conductor 134. The output of the control relay 132 is the conductor 56 which controls the cycling of solenoid valve 28.

The operation of the memory system seen in FIG. 2 may be described as follows: During the time the cam 34 is indicating that the gauging of the glass containers 14 is taking place, the switch 36 is in the position shown in FIG. 2. Under these conditions, the resistor 114 is actually grounded and may not supply the v plus voltage to the input of the NAND gate 112. Therefore, the NAND gate 112 has one zero input at this time. It is well known that the characteristics of NAND gates are such that if one of the inputs to a NAND gate is zero the output of the NAND gate must be one or high regardless of the condition of the other inputs thereto. Therefore, the conductor 122 will carry a high or one signal to one of the inputs of the second NAND gate 116. Since the conductor 40 is not connected to ground at this time, the resistor 118 will connect the voltage supply to the other input of the second NAND gate 116 therefore making the output of the second NAND gate 116 zero or low. This signal will be transmitted along the conductor 120 to the other input of the first NAND gate 112. The output of the first NAND gate 112 therefore being high or one will be transmitted along the conductor 124 to the clock inputs of all of the flip-flops. The flip-flops are all of the type which will clock or move the information therein one stage whenever a rising pulse is presented to them. Note that since all of the flip-flops are clocked by the same pulse, it is necessary that the rise time of the clock pulse be less than the total propagation time within the flip-flops. In this case, these particular flip-flops have a propagation time of approximately 150 nano seconds as a result of the master-slave relationship built into them. Therefore, the rise of the clock pulse which is generated by the first NAND gate 112 must be faster than 150 nano seconds. This will occur, as will be demonstrated, and therefore the information contained within the flip-flops 88, 92, 94, 96, 98 and 100 will be moved one stage when the clock pulse is received. Assume, for example, that a defective glass container has been detected and that this information is stored in the flip-flop 98 which would then indicate that the output Q of the flip-flop 98 is one or high. When the clock pulse occurs, this information is then shifted into the flip-flop 100 which then presents this information on its Q output terminal along the conductor 130 to the NAND gate 126. Simultaneously, the output from the NAND gate 112 will be high or one and will be carried by the conductor 128 to the NAND gate 126. This is a unique condition for the NAND gate 126, that is two simultaneously high inputs, and the output of the NAND gate 126 will be a zero signal along the conductor 134. Note that while these signals from the NAND gate 112 remain on during the entire gauging period, all of the flip-flops will be clocked only once during this time since they are responsive only to the rising voltage which occurs at the beginning of the gauging cycle or conversely at the end of the index cycle. Thus with a zero output on the conductor 134 to the control relay 132, the control relay 132 will transmit a signal to the solenoid valve 28 along the conductor 56 which will cause the tip 26 to remain extended during the gauging period. Then, during the next index cycle, the glass container that was so held will be rejected by the diverter bar 18. At the end of the gauging cycle, the switch 34 will move from contact with the conductor 41 to contact with the conductor 40. When this occurs, it is desired to have a very sharp transition to give the fast rise time necessary to prevent spurious clocking of the flip-flops within the system. Also, it is desirable to avoid ambiguous signals resulting from possible bouncing of the contacts within the switch 36. Therefore, note that when a wiper arm 136 within the switch 36 begins to move from the conductor 41 to the conductor 40, the output of the NAND gates 112 and 116 will not change state immediately. This is so because the NAND gate 112 will immediately see a high input through the resistor 114 to the positive voltage supply. In addition though, it will continue to see a low input along the conductor 120 from the NAND gate 116. When contact of the wiper arm is made with the conductor 40, the NAND gate 116 will then have one low input, since the resistor 118 will now be grounded, and will therefore immediately switch states since it no longer has presented to it two high inputs. Likewise, the first NAND gate 112 will also switch states immediately at this point since it will then have presented to it two high inputs, namely the input through the resistor 114 to the positive voltage supply and the now high output along the conductor 120 from the NAND gate 116. The result is a very fast switching time with a correspondingly fast rise time of the voltage and immunity from ambiguous results caused by possible bounce of the wiper arm 136 as it makes contact with the conductor 40. Since the switch 36 is a mechanical switch, there may be some vibration at the time the wiper arm 136 moves. However, as can be seen in the description of the movement of the wiper arm 136 from one position to another, once contact is made, the NAND gates 112 and 116 unambiguously switch states and will stay in the state to which they were switched unless the wiper arm 136 has sufficient momentum to make contact once again with the conductor 41. The net result is an output which is very rapid in rise time and which is immune to switch bouncing. Then, at the beginning of the next gauging cycle, the wiper arm 136 will then move from contact with the conductor 40 into contact with the conductor 41 with the result previously noted of rapidly clocking all of the flip-flops one position while not allowing the information contained therein to be moved more than one position. I have, therefore, determined that, in general, any master-slave flip-flop may serve as the information storage and transmission element so long as the clock pulse thereto may be shaped to have a rise time which is faster than the transmission time of information through the flip-flops.

What I claim is:

1. In an inspection machine for glass containers wherein glass containers are removed one at a time from a continually moving conveyor, wherein said glass containers are serially indexed through a plurality of inspection stations and wherein said inspection machine includes a bottle defect logic and detection means, having a plurality of output conductors, for generating signals on said output conductors if said inspected glass containers are determined to be defective in one or more aspects at any one of said inspection stations, an improved memory system for said inspection machine which comprises, in combination:

a plurality of master-slave type flip-flops, connected in series, said plurality of flip-flops being one more in number than the number of said inspection stations;

means for connecting an output conductor from said logic means to each one of said flip-flops except the last one of said plurality of flip-flops;

timing means for presenting a first electrical state when said inspection machine is inspecting and a second electrical state when said inspection machine is in its index cycle;

electronic clock circuit means, connected to said timing means and each of said flip-flops, for generating a clock pulse, having a rise time faster than the information transfer time through said flip-flops, in response to the transition of said timing means from said second electrical state to said first electrical state; and electronic output circuit means, connected to said clock circuit means and the output of the last one of said flip-flops, for generating a signal when said last flip-flop carries a signal indicating the presence of a defective glass container and when said clock pulse is present.

2. The improvement of claim 1 which further includes:

means responsive to a signal from said output circuit means for causing rejection of a defective glass container.

3. The improvement of claim 1 wherein said means for presenting a first and a second electrical state comprises:

a rotary cam; and a switch operated by said cam, said cam being contoured to place said switch in a first electrical state when said inspection machine is inspecting and in a second electrical state when said inspection machine is indexing.

4. The improvement of claim 1 wherein said electronic clock circuit means comprises:

a first NAND gate having a first input terminal connected to ground through said timing means when said inspection machine is gauging, a second input terminal and an output terminal connected to a clock input terminal of each one of said plurality of flip-flops and further connected to said electronic output circuit means;

a second NAND gate having a first input terminal connected to ground through said timing means when said inspection machine is in its index cycle, a second input terminal connected to the output terminal of said first NAND gate, and an output terminal connected to said second input terminal of said first NAND gate;

a voltage supply;

a first resistor connecting said voltage supply to said first input terminal of said first NAND gate; and a second resistor connecting said voltage supply to said first input terminal of said second NAND gate.

5. The improvement of claim 1 wherein said plurality of flip-flops each includes a direct set input terminal and wherein said means for connecting said logic means to each of said flip-flops comprises:

a plurality of optical isolators, equal in number to the number of inspection stations, one optical isolator being uniquely associated with each one of said inspection stations, said optical isolators generating an output signal when the inspection station with which it is associated detects a defective glass container as determined by a signal from said bottle defect logic and detection means; and a plurality of electrical conductors for conducting a signal from the optical isolator associated with a particular inspection station to the direct set input of one of said flip-flops, the connections being such that the first one of said flip-flops is associated with the first one of said inspection stations and the Nth one of said flip-flops is associated with the Nth one of said inspection stations.

6. A method for retaining memory of a defective glass container during the entire cycle of a glass container inspection machine which indexes glass containers through a plurality of inspection stations and generates a defect signal when a glass container fails to pass the inspection performed at any one of said plurality of inspection stations, which comprises the steps of:

loading a defect signal from any one of said inspection stations into a master-slave type flip-flop uniquely associated with that one of said inspection stations;

presenting a first electrical state when said inspection machine is inspecting;

presenting a second electrical state when said inspection machine is in its index cycle;

generating a clock pulse, in response to the transition from said second electrical state to said first electrical state, having a rise time faster than the information transfer time through said flip-flop;

shifting any information carried by said first mentioned flip-flop into a second master-slave type flip-flop uniquely associated with the next one in sequence of said inspection stations in response to said clock pulse;

continuing to shift information relative to a defective glass container in response to successive clock pulses as said glass container is indexed from inspection station to inspection station;

shifting any information carried by a flip-flop associated with the last one of said inspection stations into an output master-slave type flip-flop in response to said clock pulse; and rejecting any glass containers causing a signal to be carried by said output flip-flop.

* * * * *